(12) United States Patent
DeLegge et al.

(10) Patent No.: US 8,968,248 B2
(45) Date of Patent: *Mar. 3, 2015

(54) PEG TUBE WITH WIRELESS PULL TIP

(75) Inventors: Rebecca L. DeLegge, Mt. Pleasant, SC (US); Andrye B. McCollough, Oak Ridge, NC (US); Hilbert D. Brown, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 868 days.

This patent is subject to a terminal disclaimer.

(21) Appl. No.: 13/162,816

(22) Filed: Jun. 17, 2011

(65) Prior Publication Data

US 2012/0016298 A1 Jan. 19, 2012

Related U.S. Application Data

(63) Continuation of application No. 11/513,548, filed on Aug. 31, 2006, now Pat. No. 7,976,495.

(60) Provisional application No. 60/713,087, filed on Aug. 31, 2005, provisional application No. 61/408,877, filed on Nov. 1, 2010.

(51) Int. Cl.
*A61M 5/178* (2006.01)
*A61B 17/34* (2006.01)
(Continued)

(52) U.S. Cl.
CPC ......... *A61B 17/3415* (2013.01); *A61J 15/0015* (2013.01); *A61M 39/0247* (2013.01);
(Continued)

(58) Field of Classification Search
CPC ... A61J 15/00; A61J 15/0015; A61J 15/0038; A61J 15/0026; A61J 15/0042; A61B 17/3415

USPC ........... 604/164.01, 270, 910, 104, 190, 191, 604/533–539, 103.04, 164.02, 174, 175, 604/95.04; 606/108

See application file for complete search history.

(56) References Cited

U.S. PATENT DOCUMENTS 4,573,576 A * 3/1986 Krol .............................. 206/471
4,752,292 A * 6/1988 Lopez et al. .................. 604/244
(Continued)

FOREIGN PATENT DOCUMENTS

EP 1 371 320 A3 12/2003
WO WO 03/103566 A1 12/2003
(Continued)

OTHER PUBLICATIONS

Notification of Transmittal of the International Search Report and the Written Opinion of the International Searching Authority, or the Declaration, dated Jan. 18, 2012, for PCT/US2011/058241, 4p.

*Primary Examiner* — Kevin C Sirmons
*Assistant Examiner* — Pritesh Patel
(74) *Attorney, Agent, or Firm* — Brinks Gilson & Lione (57) ABSTRACT

A feeding tube and method for introducing a feeding tube within the gastrointestinal tract of a patient, whereby the feeding tube is introduced by using a variation of the Ponsky "pull" method of feeding tube placement. The feeding tube comprises an elongate shaft having a distal end and proximal end. The feeding tube also comprises a coupling structure for coupling the feeding tube to a pull wire, the coupling structure be proximal of the distal end of the feeding tube shaft. The feeding tube further comprises a guiding structure for aligning the pull wire with the distal end of the shaft. The feeding tube is introduced within the patient by attaching the previously placed pull wire to the coupling and guiding structures of the feeding tube, and then pulling the pull wire so as to pull the feeding tube into and through the gastrointestinal tract of the patient.

16 Claims, 11 Drawing Sheets

(51) Int. Cl.
*A61J 15/00* (2006.01)
*A61M 39/02* (2006.01)

(52) U.S. Cl.
CPC .......... *A61J15/0061* (2013.01); *A61J 15/0034* (2013.01); *A61J 15/0019* (2013.01); *A61M 2039/0255* (2013.01)
USPC ..................................... 604/164.02; 604/910

(56) References Cited

U.S. PATENT DOCUMENTS

| | | |
|---|---|---|
| 4,758,219 A | 7/1988 | Sacks et al. |
| 4,981,471 A | 1/1991 | Quinn et al. |
| 6,106,487 A * | 8/2000 | Duane et al. .................. 600/585 |
| 6,348,045 B1 * | 2/2002 | Malonek et al. .............. 604/270 |
| 6,464,686 B1 * | 10/2002 | O'Hara et al. ................ 604/539 |
| 6,685,713 B1 * | 2/2004 | Ahmed ......................... 606/140 |
| 2003/0220334 A1 | 11/2003 | Wender et al. |
| 2004/0044330 A1 * | 3/2004 | Li et al. ......................... 604/535 |
| 2005/0020875 A1 | 1/2005 | Delegge |
| 2007/0078430 A1 | 4/2007 | Adams |

FOREIGN PATENT DOCUMENTS

| | | |
|---|---|---|
| WO | WO 2005/074819 A3 | 8/2005 |
| WO | WO 2007/027920 A1 | 3/2007 |

* cited by examiner

PEG TUBE WITH WIRELESS PULL TIP

RELATED APPLICATION

This application is a continuation-in-part of U.S. application Ser. No. 11/513,548, filed Aug. 31, 2006, and titled "Peg Tube With Wireless Pull Tip", which claims the benefit of priority from U.S. Provisional Application No. 60/713,087, filed Aug. 31, 2005, and titled "Wireless Pull Tip", the contents of which is incorporated herein by reference. This application also claims the benefit of priority from U.S. Provisional Application No. 61/408,877, filed Nov. 1, 2010, and titled "Peg Tube With Wireless Pull Tip", the contents of which is incorporated herein by reference.

TECHNICAL FIELD

The present invention relates to medical devices, and more particularly to feeding tubes for delivery of nutritional products to the intestinal tract and methods for placement of feeding tubes therein.

BACKGROUND OF THE INVENTION

Patients for which normal ingestion of food becomes difficult or impossible may require placement of a feeding tube to assist in providing their nutritional needs. For some individuals, such as comatose patients, stroke victims, or those with a compromised gastrointestinal tract, this may require placement of a tube that is introduced percutaneously into the stomach for delivery of nutritional products directly into the stomach or jejunum. The procedure, known as a Percutaneous Endoscopic Gastrostomy (PEG), involves the introduction of an endoscope into the stomach, while the desired site where the stoma is to be created is indicated from above by depressing the abdomen. Transillumination may also be utilized to locate the desired site through the abdominal wall. A sheathed needle or trocar punctures the abdominal wall and enters the stomach, creating a stoma. The needle is removed and a looped insertion or pull wire is introduced through the sheath where it is grasped by a snare or forceps deployed from the working channel of the endoscope. Once it is captured, the insertion wire is pulled into the working channel of the endoscope. The endoscope is then withdrawn from the patient via the oral cavity, pulling the insertion wire with it.

In the standard Ponsky method (or "pull" method), the percutaneous gastrostomy feeding tube is coupled to the portion of the insertion wire exiting the patient's mouth. More specifically, the loop of the insertion wire is knotted or tied to a loop attached to the distal end of the gastrostomy feeding tube. With the insertion wire now tethered to the gastrostomy feeding tube, the endoscopist retracts the portion of the insertion wire exiting the stoma, thereby pulling the gastrostomy feeding tube into the patient's mouth and towards the stomach. With continued retraction of the insertion wire, the distal end of the gastrostomy feeding tube is pulled out through the stoma. The gastrostomy feeding tube typically includes a tapered dilator portion to aid its passage through the stoma. Once the feeding tube has been properly positioned with the proximal end cap or bolster of the feeding tube against the internal wall of the stomach, it is secured by an external bolster positioned against the outside of the abdomen wall. The endoscope is typically reintroduced into the stomach to check the internal position of the feeding tube before the external bolster is secured. The dilator portion of the feeding tube, including the insertion wire tied thereto, is then cut away and removed and an adapter compatible with standardized feeding pumps and syringes is attached.

Conventional gastrostomy feeding tubes specifically configured for placement by the standard "pull" method have a number of drawbacks. For example, conventional "pull" type gastrostomy feeding tubes typically have a loop of wire affixed to the distal end of the dilator for attachment to the insertion wire. This attachment loop may be subjected to significant pulling forces as the gastrostomy feeding tube is pulled, via the insertion wire, through the mouth, esophagus and stomach of the patient. The manner of securing the attachment loop to the dilator must therefore be substantial, which may necessitate a larger dilator than would otherwise be desired. In addition, the attachment loop may become detached from the dilator during the "pull" method of insertion, thereby necessitating that the feeding tube be removed and the placement procedure be re-started with a new feeding tube. There is also the possibility that the insertion wire may separate from the feeding tube attachment loop during the placement procedure. For example, the knot that is used to secure the loop of the insertion wire to the attachment loop may become untied, thereby necessitating that the procedure be started over by re-advancing the end of the insertion wire out of the patient's mouth and re-tying it to the feeding tube. Moreover, the step of securely tying the insertion wire to the feeding tube attachment loop may be time consuming and difficult. Finally, the knot between the insertion wire and the feeding tube tends to snag on or irritate the tissue of the esophagus, stomach, and stoma as it is being pulled therethrough.

What is needed is a gastrostomy feeding tube that can be introduced using the "pull" method, and which can be quickly and securely attached to a looped insertion or pull wire, which can be secured to the pull wire without tying or knotting the pull wire to the feeding tube, and which does not include or rely on a loop of wire affixed to the dilator portion of the feeding tube.

SUMMARY OF THE INVENTION

The foregoing problems are solved and a technical advance is achieved with an illustrative feeding tube and method for introducing a feeding tube within the gastrointestinal tract of a patient, whereby the feeding tube is introduced using a variation of the Ponsky "pull" method of feeding tube placement. The feeding tube comprises an elongate shaft having a distal end and proximal end. The feeding tube also comprises a coupling structure for coupling the feeding tube to a pull wire, the coupling structure be proximal of the distal end of the feeding tube shaft. The feeding tube further comprises a guiding structure for aligning the pull wire with the distal end of the shaft. The feeding tube is introduced within the patient by attaching the previously placed pull wire to the coupling and guiding structures of the feeding tube, and then pulling the pull wire so as to pull the feeding tube into and through the gastrointestinal tract of the patient. The coupling and guiding structures eliminate the need for a separate attachment loop affixed to the distal end of the feeding tube. The coupling and guiding structures also eliminate the difficulties and problems associated with tying the pull wire to an attachment loop on the feeding tube.

In one aspect of the invention, the coupling structure comprises a portion of the feeding tube, such as the dilator, about which the elongate pull member is disposed. In other aspects of the invention, the coupling structure comprises a hook or prong structure for engaging the loop of the pull wire. In still other aspects of the invention, the coupling structure comprises a clip mechanism that is movable between an open position and a closed position, the open position permitting the pull wire to be attached to the feeding tube and the closed position preventing the pull wire from becoming disengaged from the feeding tube.

In another aspect of the invention, the feeding tube comprises a guiding structure for directing the pull wire towards the distal end of the feeding tube, and for aligning the pull wire with the distal end of the feeding tube. In certain aspects of the invention, the guiding structure comprises a passageway or lumen extending through a portion of the feeding tube. In other aspects of the invention, the guiding structure comprises one or more grooves disposed in the side of the feeding tube.

The feeding tube is introduced within the patient by securing the looped end of a previously placed pull wire to the coupling and guiding structures of the feeding tube. More specifically, the feeding tube is secured to the portion of the pull wire extending out of the patient's mouth. The portion of the pull wire extending out through the stoma of the patient, which is opposite of the looped portion, is then pulled so as to pull the feeding tube through the mouth of the patient and into the gastrointestinal tract using a variation of the Ponsky "pull" method of placement. Other aspects of the procedure for the final positioning and placement of the feeding tube according to the present invention are similar to the procedure used for final positioning and placement of a standard feeding tube.

These and other advantages, as well as the invention itself, will become apparent in the details of construction and operation as more fully described below. Moreover, it should be appreciated that several aspects of the invention can be used with other types of stent delivery catheters or medical devices.

DESCRIPTION OF THE INVENTION

Various embodiments of the feeding tube 10 according to the present invention are shown in FIGS. 1-19. In general, the feeding tube 10 comprises an elongate tubular shaft 12 having a proximal end 14 and a distal end 16. A feeding lumen 18 extends through at least a portion of the shaft 12 and provides a passageway for the delivery of nutritional products or medications directly into the gastrointestinal tract of the patient. An exemplary embodiment of a feeding tube according to the present invention is a percutaneous endoscopic gastrostomy (or PEG) feeding tube 20 (shown in FIG. 1) that is positioned through the stomach and abdominal walls of the patient. The PEG feeding tube 20 allows the delivery of nutritional products or medications directly into the patient's stomach. As will be explained in greater detail below, the PEG feeding tube 20 is introduced into and placed within the patient by coupling the feeding tube 20 to a pull wire 22 that has been previously placed through the gastrointestinal tract of a patient, and then pulling the pull wire 22 so as to pull the feeding tube 20 into the patient's stomach using a variation of the Ponsky "pull" method of feeding tube placement.

In general, the feeding tube 10 comprises a coupling structure 26 for receiving and securing the loop 24 of an elongate pull wire 22 to the feeding tube. The coupling structure 26 is disposed along the distal portion of the elongate shaft 12 at a location that is proximal to the distal end 16. The feeding tube 10 further comprises a guiding structure 28 for directing the pull wire toward the distal end 16 of the feeding tube 10 so as to maintain the pull wire 22 in substantial alignment with the distal end of the feeding tube 10 during the placement procedure. As will be explained in greater detail below, the coupling and guiding structures 26, 28 eliminate the need for a separate loop affixed to the distal end of the feeding tube for attachment to the pull wire, and also eliminate the difficulties and problems associated with tying the pull wire to an attachment loop on the feeding tube.

Figure 1:
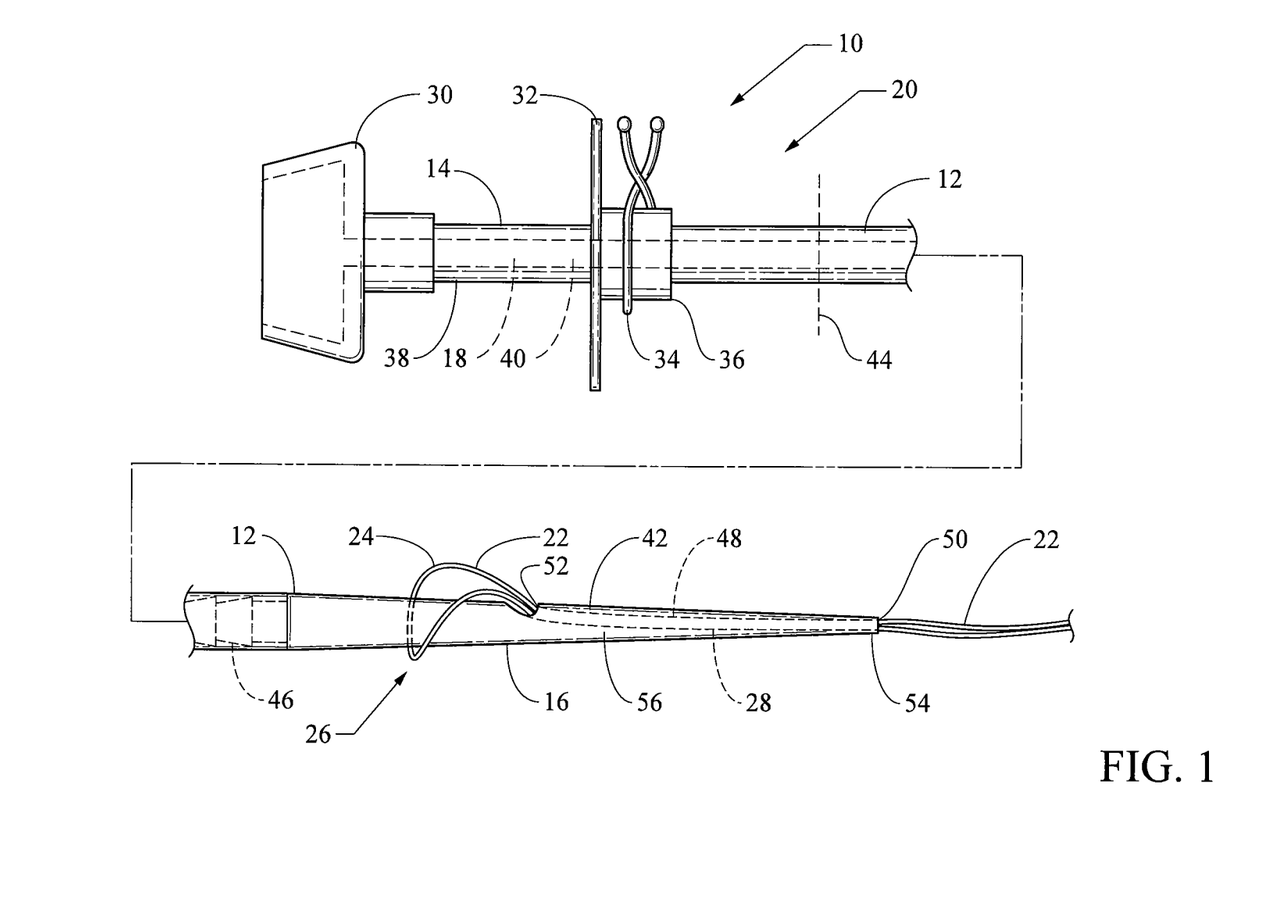
FIG. 1 is a side view of one embodiment of the feeding tube of the present invention, and in particular a short wire gastrostomy (or PEG) feeding tube.

In the embodiment illustrated in FIG. 1, the feeding tube 10 comprises a pull type percutaneous endoscopic gastrostomy (or PEG) feeding tube 20 that can be introduced within the patient with a looped pull wire 22 using a variation of the Ponsky "pull" method of introduction. The PEG feeding tube 20 comprises an elongate shaft 12 having a distal end 16 and a proximal end 14. An internal bolster (or bumper) 30 is affixed to the proximal end 14 of the shaft 12 and is configured to engage the interior surface of the stomach wall. In the particular embodiment illustrated, the overall length of the shaft 12 is between 105 and 145 cm. An exterior bolster 32 is provided and is configured to attach to the shaft 12 so as to engage the exterior surface of the abdomen. In the embodiment illustrated, the external bolster 32 is secured to the shaft 12 by a spring clamp 34 that presses the sleeve 36 of the external bolster 32 into frictional engagement with the exterior surface of the shaft 12. However, other types and designs of internal and external bolsters 30, 32 may be employed. For example, internal bolster 30 may comprise an inflatable balloon or other expandable structure.

The proximal portion of the shaft 12 comprises a feeding catheter 38 having a feeding lumen 40 disposed therethrough. In the particular embodiment illustrated, the feeding catheter 38 comprises an 18-24 French tube having a 4-5.5 mm diameter feeding lumen 40. The distal portion of the shaft 12 comprises a removable lead catheter 42, commonly referred to as a dilator, which is preferably tapered to facilitate ingress through the gastrointestinal tract of the patient. The dilator 42 and the feeding catheter 38 may be manufactured as separate components and joined together via an attachment structure, such as barbed connector 46, or may be manufactured as a unitary structure. As will be explained in greater detail below, the dilator 42 is removed from the feeding catheter 38 by, for example, severing the shaft 12 along cut line 44.

In the embodiment illustrated in FIG. 1, the guiding structure 28 comprises a passageway or lumen 48 which extends through a portion of the elongate shaft 12, and in particular, through a portion of the dilator 42. The lumen 48 is sized to permit a pull wire 22 to pass therethrough and extends between a distal opening or port 50 near the distal end 16 of the shaft 12 and a proximal opening or port 52 spaced distally from the distal end 6 of the shaft 12. In the particular embodiment illustrated, the distal opening 50 is disposed in the distal tip 54 of the dilator 42 and the proximal opening 52 extends through a side wall 56 of the dilator 42. In the embodiment illustrated, the proximal opening 52 is spaced approximately 5-10 cm from the distal opening 50.

In the embodiment illustrated in FIG. 1, the coupling structure 26 comprises a portion of the dilator 42 about which the loop 24 of the pull wire 22 is disposed. More specifically, the coupling structure 26 comprises the exterior surface of the side wall 56 that is engaged by the interior surface of the loop 24 of the pull wire 22 as the pull wire 22 is pulled distally through the guiding structure 28. The coupling structure 26 is located adjacent to the proximal opening 52 of the guiding structure 28.

The coupling and guiding structures 26, 28 eliminate the need for a separate loop affixed to the distal end of the feeding tube for attachment to the pull wire 22, and also eliminate the difficulties and problems associated with tying the pull wire 22 to an attachment loop on the feeding tube. More specifically, the coupling structure 26 provides an efficient method for securing the loop 24 of the pull wire 22 to the dilator portion without need to tie the pull wire 22 to any portion of the feeding tube 10. The coupling structure 26 also provides for an attachment location that is spaced proximally from the distal tip 54 of the dilator 42, thereby allowing for a reduction in size of the distal tip 54. Moving the spacing the attachment location proximally from the distal tip 54 also reduces the likelihood that the feeding tube 10 will inadvertently separate from the pull wire 22 during the placement procedure.

The guiding structure 28 directs the pull wire 22 from the coupling structure 26 to the distal tip 54 of the dilator 42. More specifically, the guiding structure 28 aligns the pull wire 22 with the distal tip 54. In other words, the guiding structure 28 directs the pulling force (applied by the pull wire 22 to the dilator 42) through the distal tip 54, which helps to guide the distal tip 54 along a central pathway as the feeding tube is being pulled through the patient's gastrointestinal tract. Guiding the distal tip 54 along a central pathway reduces the chance of snagging and irritation to the tissue of bodily lumen that may be caused by the distal tip 54 during its introduction. This also reduces the frictional forces that are encountered by the feeding tube 10 during its introduction and placement, thereby reducing the amount of pulling force required to pull the feeding into and through the patient.

Figure 2:
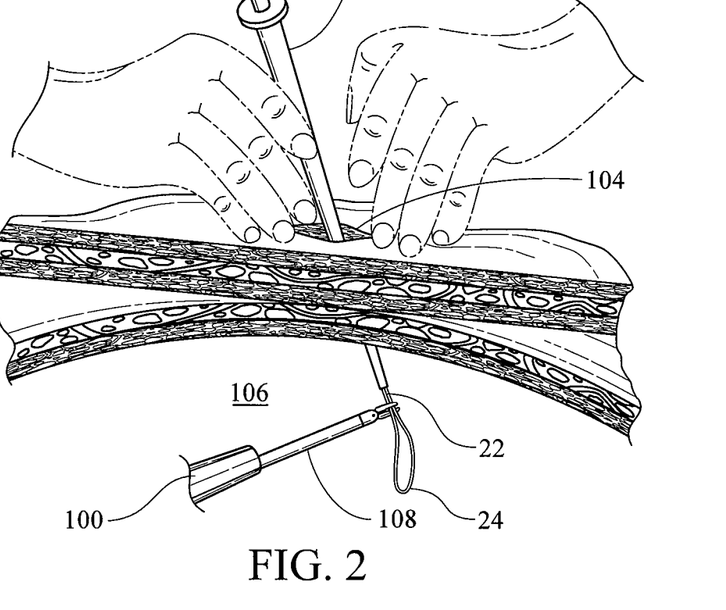
FIGS. 2-7 illustrate successive steps in an exemplary method of introducing and placing the embodiment of the feeding tube of FIG. 1 into the gastric lumen of a patient.

The PEG feeding tube 20 of FIG. 1 is introduced within the patient using a variation of the standard Ponsky "pull" method of placement. An exemplary embodiment of this procedure is illustrated in FIGS. 2-7. With reference to FIG. 2, an endoscope 100 is introduced through the mouth and into the stomach of the patient. A standard Esophagogastroduodenoscopy (EGD) is then typically performed with the endoscope. An EGD is an examination of the lining of the esophagus, stomach, and upper duodenum with the endoscope's camera. The endoscope is then used to identify the desired site where the stoma is to be created. The site is typically identified by depressing the abdomen from outside the patient. Transillumination may also be utilized to locate the desired site through the abdominal wall. For example, the room lights are dimmed so that the light emitted from the end of the endoscope can be seen from outside the patient (i.e., through the stomach and abdominal wall tissue). Once the target site has been identified, a trocar or sheathed needle 102 punctures the abdominal and stomach walls to create a stoma 104, with the distal end of needle 102 entering the interior of the stomach cavity 106. The needle 102 is removed and a pull wire 22 is introduced through the sheath and into the stomach cavity 106. The loop 24 or distal end of the pull wire 22 is then grasped by grasping device 108, such as a snare or forceps, which is deployed from the working channel of the endoscope 100. Once end of the pull wire 22 is captured, the grasping device 108 is retracted so as to pull distal end of the pull wire 22 into the working channel of the endoscope 100. The endoscope 100 is then withdrawn from the patient via the oral cavity, pulling the distal end of the pull wire 22 with it.

Figure 3:
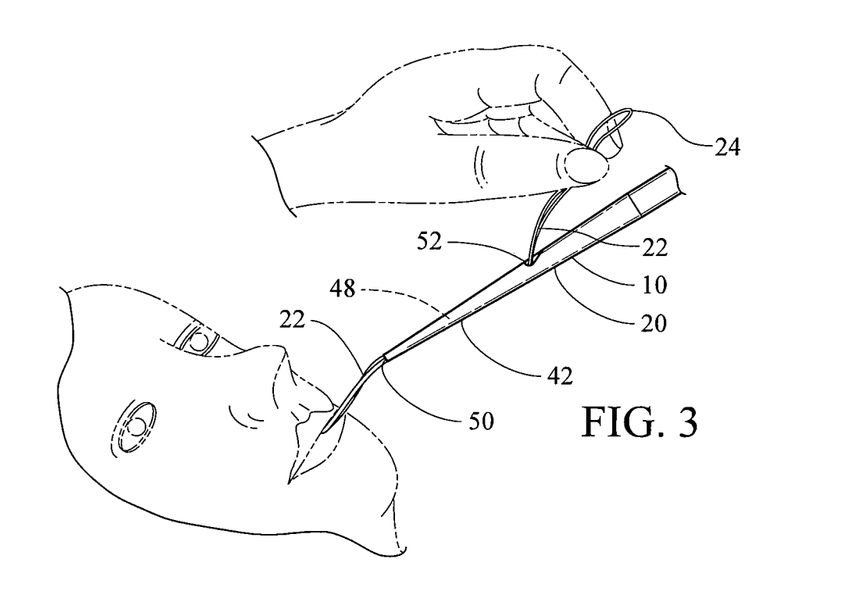
Figure 4:
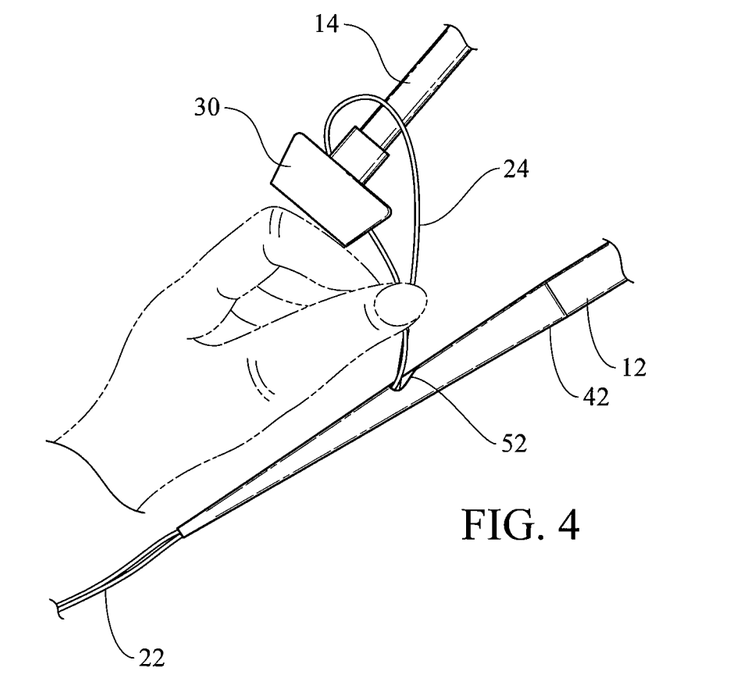
Figure 5:
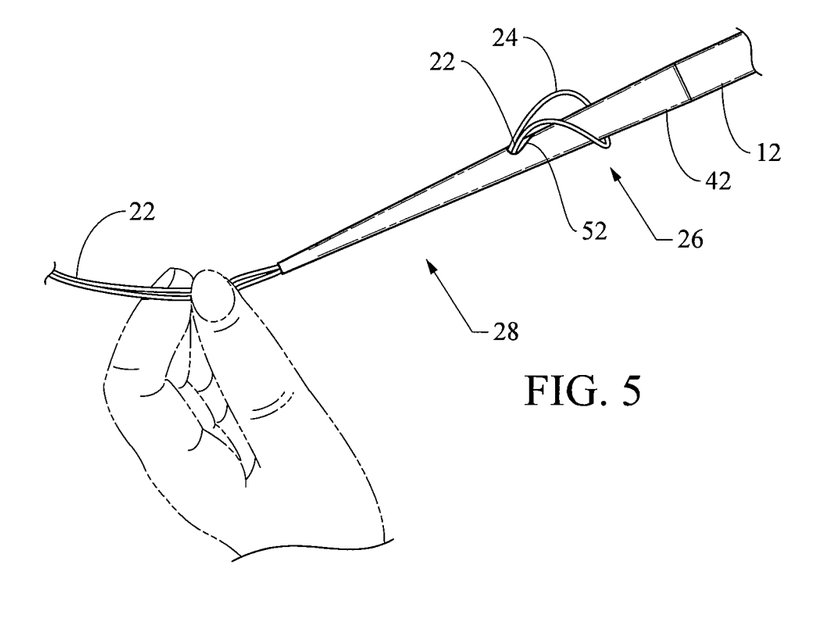

With reference to FIG. 3, the PEG feeding tube 20 is introduced within the patient by first coupling the distal end of the feeding tube shaft 12 to the distal end of the pull wire 22. In particular, the portion of the pull wire 22 extending out from the patient's mouth (i.e., loop 24) is inserted in through the distal opening 50, along the lumen 48, and out through proximal opening 52 of the guiding structure 28 of the dilator 42. The portion of the pull wire 22 (i.e., loop 24) extending out through the proximal opening 52 is then grasped and, as shown in FIG. 4, the loop 24 is passed over the internal bolster 30 on the proximal end 14 of the feeding tube 20. The loop 24 of the pull wire 22 is then maneuvered along the shaft 12 of the feeding tube 20 until it is positioned near the proximal opening 52 and the proximal end of guiding structure 28, as shown in FIG. 5. The pull wire 22 is then pulled in a distal direction (relative to feeding tube 10) so as to remove any slack in the portion of the pull wire 22 extending from proximal opening 52 and snug-up the loop 24 about the body of the dilator 42.

Figure 6:
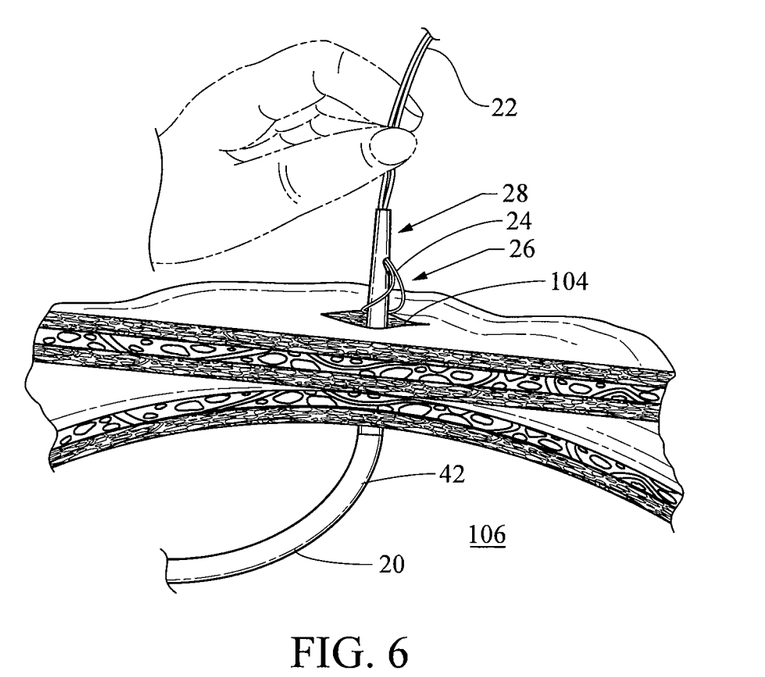
Figure 7:
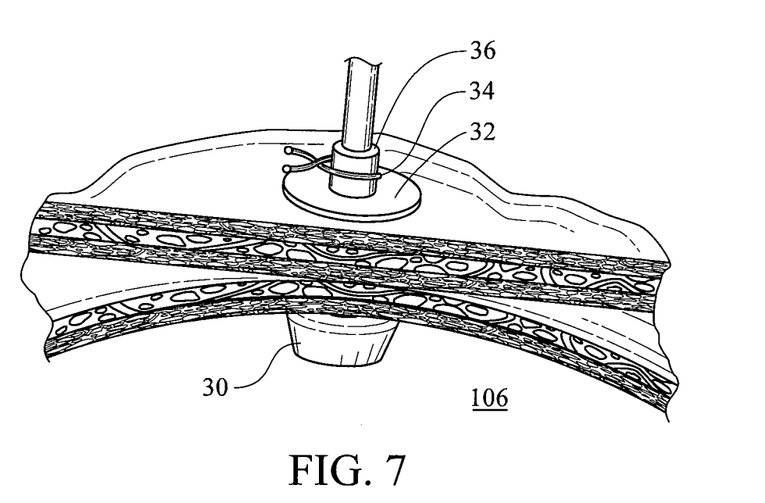

With reference to FIG. 6, the proximal end of the pull wire 22, i.e., the portion extending out of the stoma 104, is then grasped and pulled away from the patient. This pulling action pulls the dilator 42 of the PEG feeding tube 20 to be pulled through the mouth and into the gastrointestinal tract of the patient (see FIG. 3). With continued pulling of the pull wire 22, the dilator 42 of the feeding tube 20 is pulled into the patient's stomach 106. As illustrated in FIG. 6, further retraction of the pull wire 22 causes the distal end 16 of the shaft 12 (i.e., dilator 42) to be pulled out through the stoma 104. As noted above, the dilator 42 of the feeding tube 20 preferably includes a tapered dilator portion (see FIG. 1) to aid its passage through the stoma 104. Once the lead dilator 42 passes out through the stoma 104, the pull wire 22 may be removed (disengaged) from the feeding tube 20. The endoscope 100 may then be reintroduced into the stomach cavity 106 to check the position of the feeding tube 20 (i.e., the position of the internal bolster 30). As illustrated in FIG. 7, once the feeding tube 20 has been properly positioned with the internal bolster 30 of the feeding tube against the internal wall of the stomach, it is secured by an external bolster 32 secured to the shaft 12 and positioned against the outside of the abdomen wall. The dilator 42 is then cut away and removed and an adapter compatible with standardized feeding pumps and syringes is attached. Other aspects of the procedure for the introduction and placement of the PEG feeding tube 20 not described herein are similar to the standard Ponsky "pull" procedure for introduction and placement of a standard PEG tubes and have not been repeated here.

Figure 8:
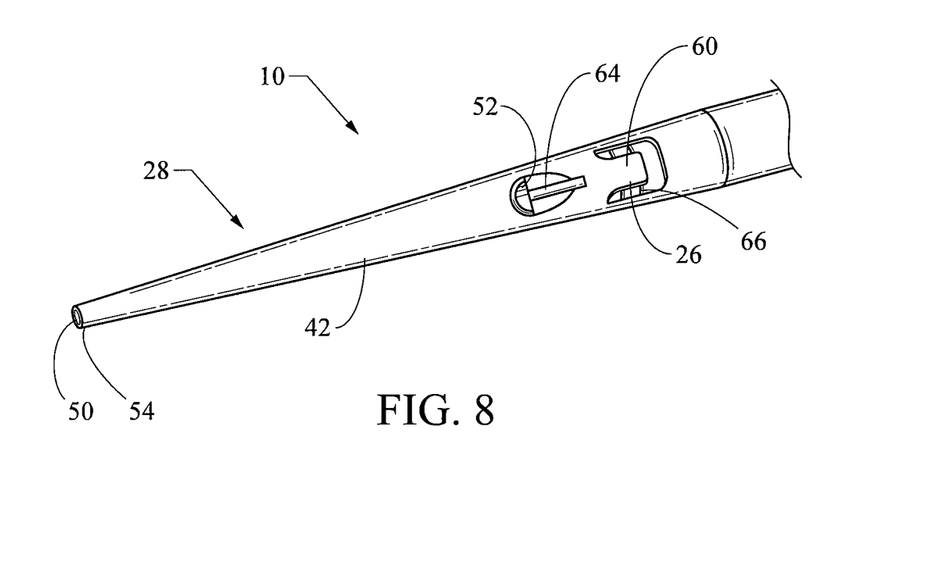
FIG. 8 is a perspective view of the dilator portion of another embodiment of the feeding tube of the present invention.
Figure 9:
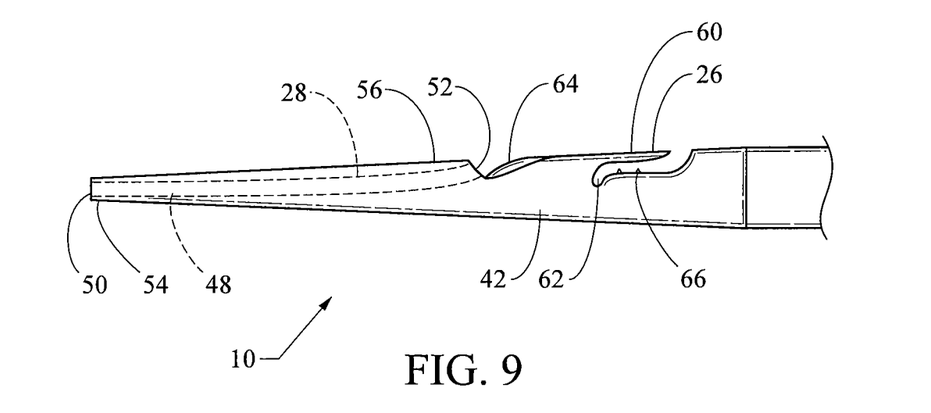
FIG. 9 is a side view of the embodiment of the feeding tube of FIG. 8.

An alternative embodiment of the feeding tube 10 according to the present invention is illustrated in FIGS. 8 and 9, wherein FIG. 8 is a perspective view and FIG. 9 is a side view of the dilator portion 42 of the feeding tube 10. This particular embodiment comprises a guiding structure 28 that is similar to that of the embodiment illustrated in FIG. 1. More specifically, the guiding structure 28 comprises a lumen 48 that extends through an internal portion of the dilator 42. The lumen 48 extends between a distal opening 50 in the distal tip 54 of the dilator 42 and a proximal opening 52 through the side wall 56 of the dilator 42, and is configured to allow the passage of a pull wire 22 (not shown) therethrough. However, and as best seen in FIG. 9, a portion of the side wall 56 adjacent to the proximal opening 52 has been removed to decrease the angle at which the pull wire 22 exits the proximal opening 52 relative to the central axis of the dilator 42, thereby allowing the pull wire 22 to be more closely disposed against the side wall 56 of the dilator 42. A ramp 64 is provided to help guide the pull wire 22 out of the proximal opening 52 and make it easier to be grasped by the user as it exits the proximal opening 52. In addition, the feeding tube 10 shown in FIGS. 8 and 9 has a coupling structure 26 that comprises a hook 60 formed in the side wall 56 of the dilator 42. The hook 60 projects proximally to define a cavity 62 into which the loop 24 of the pull wire 22 can be disposed. Ridges 66 may be provided along the surface of the cavity to prevent or inhibit the loop 24 of the pull wire 22 from being inadvertently removed from the cavity 62 and disengaging with the hook 60. The hook 60 allows the loop 24 of the pull wire 22 to be quickly secured to the dilator 42 of the feeding tube 10 without having to pass the loop 24 over the internal bolster 30 and the proximal end 14 of the shaft 12 (i.e., as described above in connection with FIG. 4). In the particular embodiment illustrated, the hook 60 is formed by removing material from the side wall 56 in the location of the cavity 62.

Figure 10:
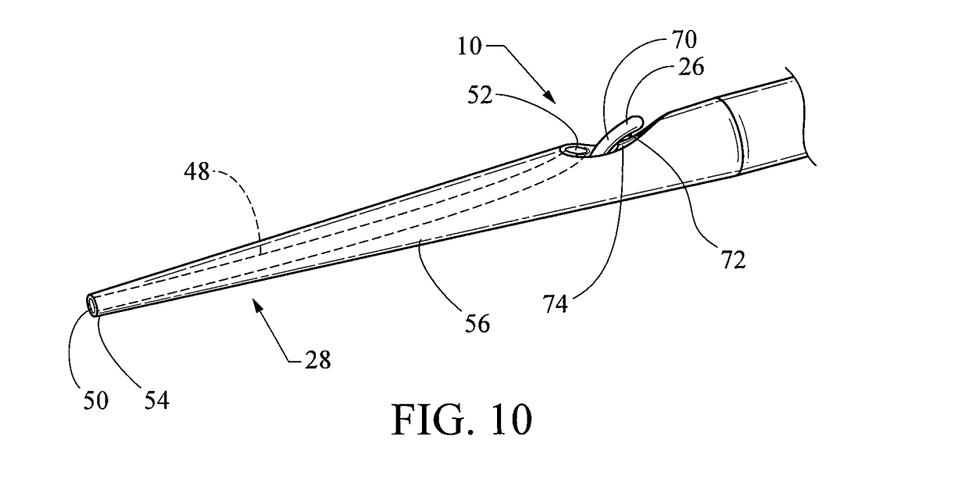
FIG. 10 is a perspective view of the dilator portion of another embodiment of the feeding tube of the present invention.

Another alternative embodiment of the feeding tube 10 according to the present invention is illustrated in FIG. 10. This particular embodiment comprises a guiding structure 28 that is similar to that of the embodiment illustrated in FIGS. 8 and 9. More specifically, the guiding structure 28 comprises a lumen 48 that extends through an internal portion of the dilator 42. The lumen 48 extends between a distal opening 50 in the distal tip 54 of the dilator 42 and a proximal opening 52 through the side wall 56 of the dilator 42, and is configured to allow the passage of a pull wire 22 (not shown) therethrough. A portion of the side wall 56 adjacent to the proximal opening 52 has also been removed to decrease the angle at which the pull wire 22 exits the proximal opening 52 relative to the central axis of the dilator 42, thereby allowing the pull wire 22 to be more closely disposed against the side wall 56 of the dilator 42. In addition, the feeding tube 10 shown in FIG. 10 has a coupling structure 26 that comprises a prong 70 affixed to the side wall 56 of the dilator 42. The prong 70 projects proximally to define a receiving area 74 between the underside of the prong 70 and the exterior surface of the dilator 42 into which the loop 24 of the pull wire 22 can be disposed. A ridge 72 may be provided along the underside of the prong 70 to prevent or inhibit the loop 24 of the pull wire 22 from being inadvertently removed from the receiving area 742 and disengaging from the prong 70. The prong 70, like hook 60 of the previous embodiment, allows the loop 24 of the pull wire 22 to be quickly secured to the dilator 42 of the feeding tube 10 without having to pass the loop 24 over the internal bolster 30 and the proximal end 14 of the shaft 12 (i.e., as described above in connection with FIG. 4). In the particular embodiment illustrated, the hook 60 is a separately formed component that is affixed to side wall 56 of the dilator 42.

Figure 11:
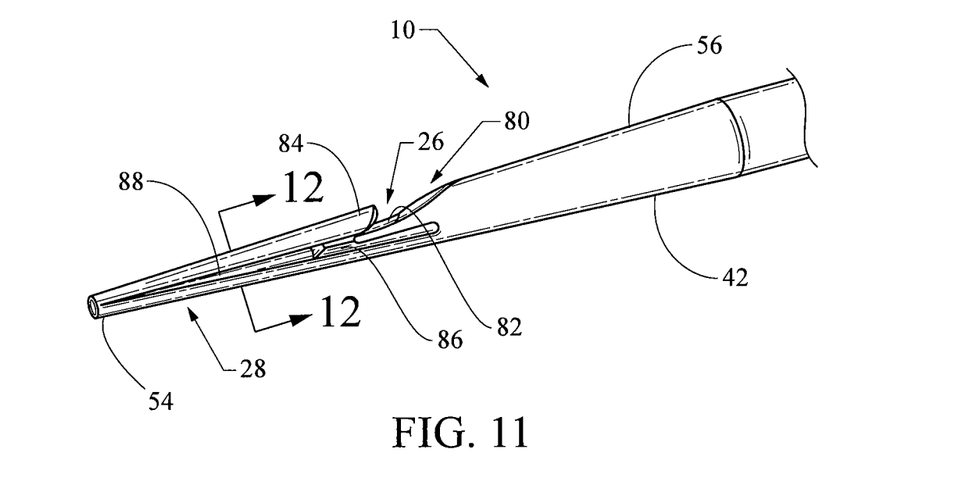
FIG. 11 is a perspective view of the dilator portion of another embodiment of the feeding tube of the present invention.
Figure 12:
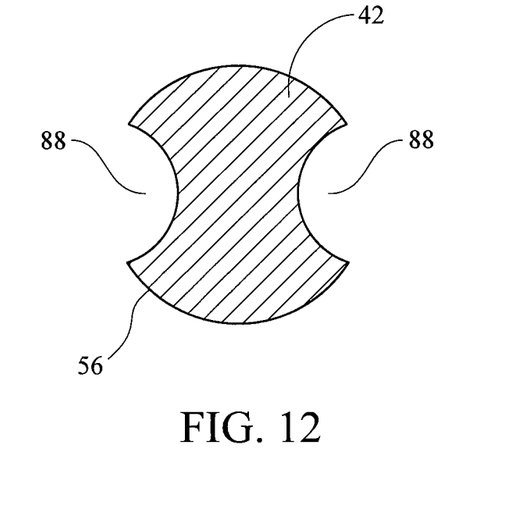
FIG. 12 is a cross-sectional view of the embodiment of the feeding tube of FIG. 11 taken along line 12-12.

Another alternative embodiment of the feeding tube 10 according to the present invention is illustrated in FIGS. 11 and 12, wherein FIG. 11 is a perspective view of the dilator 42 of the feeding tube and FIG. 12 is cross-sectional view taken along line 12-12 of FIG. 11. The coupling structure 26 of this particular embodiment comprises a clip mechanism 80 that includes a movable latch 82 that engages a stop 84, which together form a receiving area 86 configured to receive the loop 24 of a pull wire 22. More specifically, the latch 82 is movable between a closed position, shown in FIG. 10, and an open position wherein the latch 82 is spaced away from the stop 84. When in the open position, the latch 82 permits the loop 24 of a pull wire 22 to pass through the gap and into the receiving area 86. The latch 82 comprises a resilient material that is biased in the closed position, but which can be depressed into the open position by a user by, for example, depressing the latch 82 in an inward direction. The clip mechanism 80 allows the loop 24 of the pull wire 22 to be quickly secured to the dilator 42 of the feeding tube 10 without having to pass the loop 24 over the internal bolster 30 and the proximal end 14 of the shaft 12 (i.e., as described above in connection with FIG. 4).

The feeding tube 10 shown in FIGS. 11 and 12 further comprises a guiding structure 28 that comprises a pair of open channels or grooves 88 disposed on opposite sides of the dilator 42. As best seen in FIG. 11, the grooves 88 are deepest and widest near the receiving area 86 of the clip mechanism 80, and decrease in width and depth as the grooves 88 near the distal tip 54. The grooves 88 tend to direct the loop 24 of the pull wire 22 (not shown) along the side wall 56 of the dilator 42 between the coupling structure 26 and the distal tip 54. For example, as a pull force is applied by the pull wire 22 to the feeding tube 10, the resulting tension in the pull wire 22 tend to push the legs of the loop 24 of the pull wire 22 into grooves 88. As a result, the distal tip 54 will tend to be captured between the legs of the loop 24.

Figure 13:
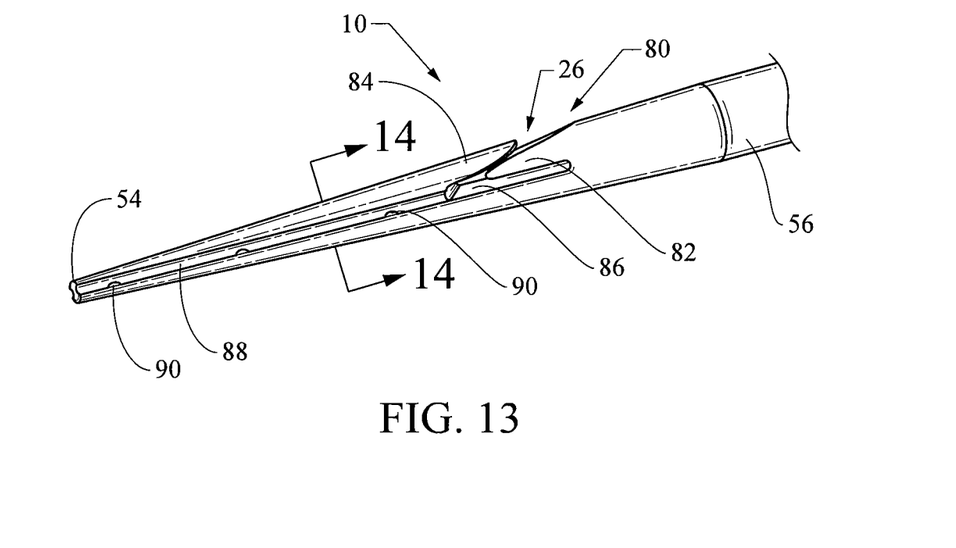
FIG. 13 is a perspective view of the dilator portion of another embodiment of the feeding tube of the present invention.
Figure 14:
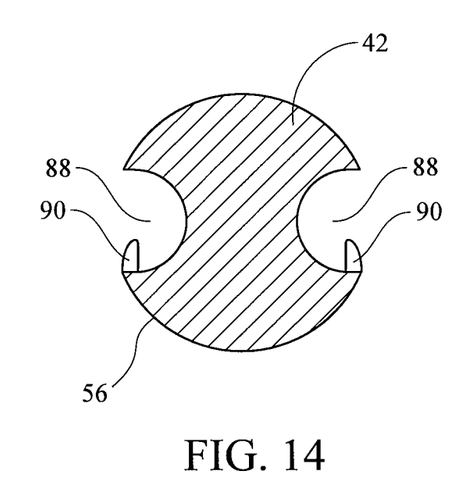
FIG. 14 is a cross-sectional view of the embodiment of the feeding tube of FIG. 13 taken along line 14-14.

Another alternative embodiment of the feeding tube 10 according to the present invention is illustrated in FIGS. 13 and 14, wherein FIG. 13 is a perspective view of the dilator 42 of the feeding tube and FIG. 14 is cross-sectional view taken along line 14-14 of FIG. 13. The coupling structure 26 of this particular embodiment is similar to that of the previous embodiment illustrated in FIGS. 11 and 12 and will therefore not be repeated here. The guiding structure 28 of this embodiment is also similar to that of the previous embodiment illustrated in FIGS. 11 and 12. However, and as best seen in FIG. 13, the grooves 88 have a substantially uniform width and depth along the length thereof. As a result, the grooves 88 for channels through the distal tip 54 of the dilator. In addition, the grooves 88 comprise a plurality of retaining bumps 90 spaced there along. As best seen in FIG. 14, the retaining bumps 90 are formed on a side wall of the groove 88 and project outwardly towards the opposite side wall. The retaining bumps 90 are configured to retain a pull wire 22 (not shown) within groove 88. More specifically, the retaining bumps 90 are configured to permit a pull wire 22 to be pushed into the groove 88, but will tend to prevent the pull wire 22 from inadvertently falling out of the groove 88. In the particular embodiment illustrated, the retaining bumps 90 include a rounded outer surface that facilitates movement of the pull wire 22 into groove 88, and a flat inner surface that tends to trap the pull wire 22 within the groove 88. The retaining bumps 90 may also be flexible or depressible to allow the pull wire 22 to be forced past the retaining bumps 90 and into the groove 88. Similar to the previous embodiment illustrated in FIGS. 11 and 12, the groves 88 tend to direct the loop 24 of the pull wire 22 along the side wall 56 of the dilator 42 between the coupling structure 26 and the distal tip 54, thereby keeping the distal tip 54 aligned with the pull wire 22.

Figure 15:
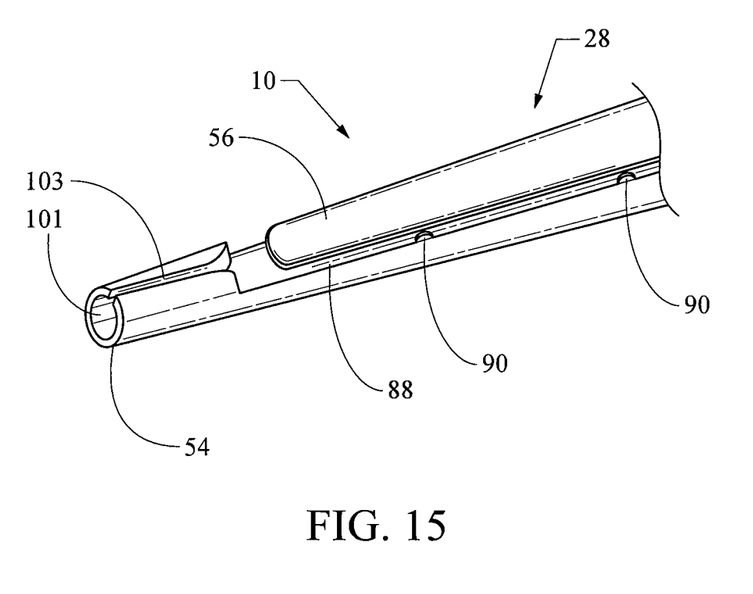
FIG. 15 and FIG. 16 are perspective views of the dilator portion of additional embodiments of the feeding tube of the present invention.

Another alternative embodiment of the feeding tube 10 according to the present invention is illustrated in FIG. 15. The coupling structure 26 is not illustrated in this embodiment, but may comprise any of the coupling structures 26 described above in connection with other embodiments of the present invention. In addition, the guiding structure 28 of this embodiment is similar to that of the embodiment shown in FIGS. 13 and 14. More specifically, the guiding structure 28 includes a pair of grooves 88 disposed along the side wall 56 of the dilator 42. The guiding structure also includes a plurality of retaining bumps 90 spaced along the grooves 88. However, this embodiment further includes a guide channel 101 through the distal tip 54 for further guiding and aligning the pull wire 22 (not shown) with the distal tip 54. A slot 103 is provided through the side wall 56 of the dilator 42 to provide access to the guide channel 101. Once the pull wire 22 is secured to the coupling structure 26 of the dilator 42, the pull wire 22 is then passed through the slot 103 and into the guide channel 101 (and the grooves 88). Because the slot 103 is approximately the same size as the diameter of the pull wire 22, the likelihood that the pull wire 22 will be inadvertently pulled out of the channel 101 is greatly reduced. In the alternative, the material adjacent to the slot 103 (i.e., the side wall 56 of the dilator 42) can be formed of a resilient or deformable material so as to permit the slot 103 to be movable between an open and closed position. For example, the slot 103 could be biased in an open positioned, then crimped to close the slot 103 once the pull wire 22 has been positioned in the guide channel 101.

Figure 16:
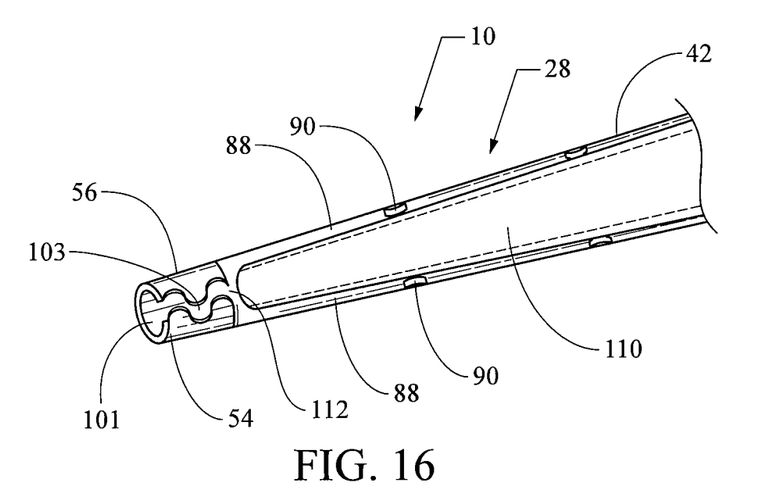

Another alternative embodiment of the feeding tube 10 according to the present invention is illustrated in FIG. 16. The coupling structure 26 is not illustrated in this embodiment, but may comprise any of the coupling structures 26 described above in connection with other embodiments of the present invention. In addition, the guiding structure 28 of this embodiment is similar to that of the embodiment shown in FIG. 15 and includes a slot 103 providing access to a guide channel 101. However, the access slot 103 of this embodiment comprises a serpentine shape that inhibits inadvertent or unintentional removal of the pull wire 22 from the guide channel 101. In addition, the guiding structure 28 of this embodiment further comprises a sliding cover 110 that may be moved in a distal direction to close off the open proximal end 112 of the access slot 103. For example, once the pull wire 22 has been passed through the access slot 103 and into the guide channel 101, the sliding cover 110 (shown in the open position in FIG. 16) may be pushed distally to block off the open end 112 of the access slot 103 and completely trap the pull wire 22 within the guide channel 101.

Figure 17:
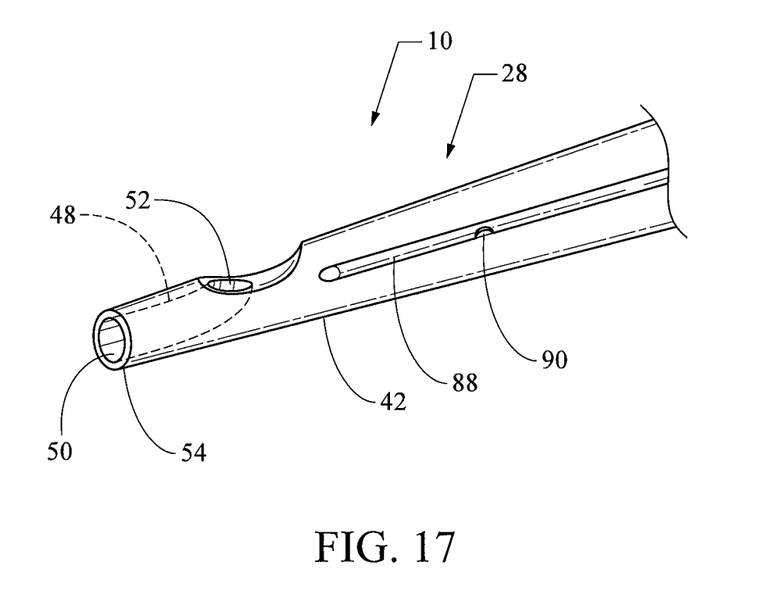
FIG. 17 is a perspective view of the dilator portion of another embodiment of the feeding tube of the present invention.

Another alternative embodiment of the feeding tube 10 according to the present invention is illustrated in FIG. 17, which comprises a guiding structure 28 that includes a lumen 48 extending between a distal opening 50 and a proximal opening 52, and further includes a pair of grooves 88 with retaining bumps 90. In other words, the embodiment shown in FIG. 17 includes a combination of guiding structure features shown in the embodiments illustrated in FIGS. 8-14.

Figure 18:
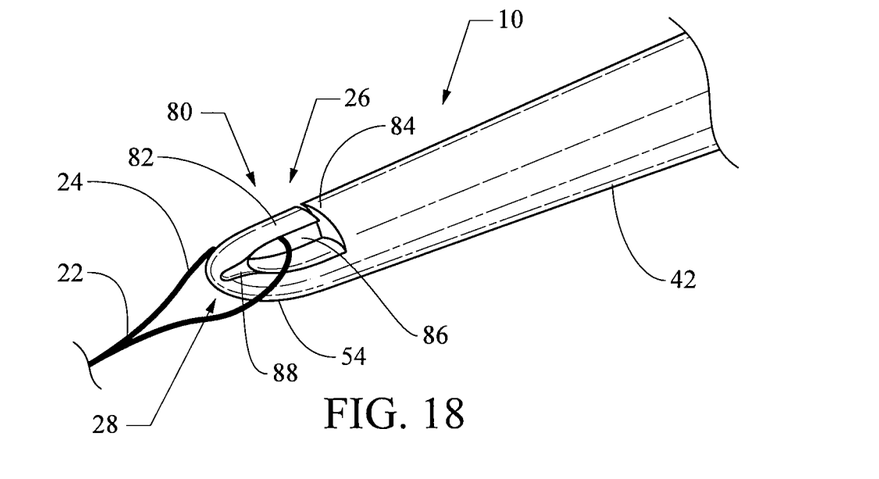
FIG. 18 is a perspective view of the dilator portion of another embodiment of the feeding tube of the present invention.
Figure 19:
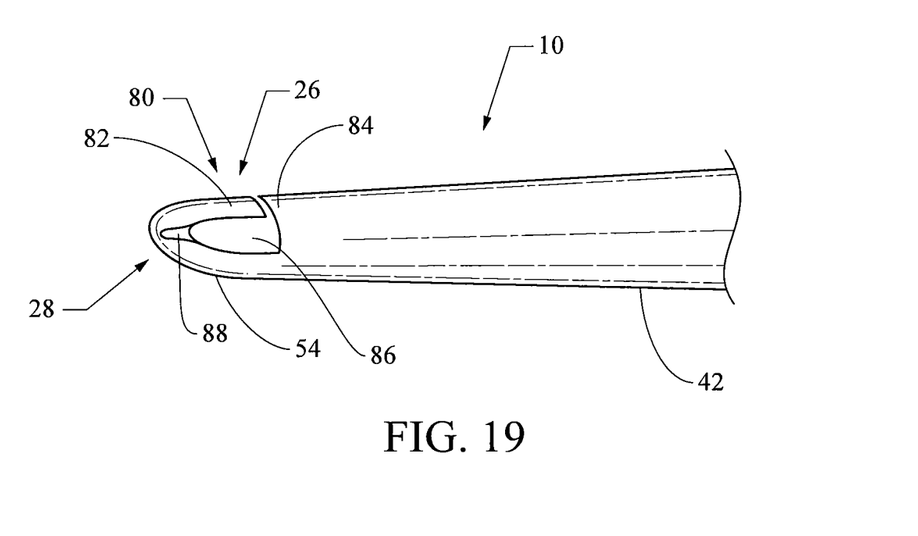
FIG. 19 is a side view of the embodiment of the feeding tube of FIG. 18.

Another alternative embodiment of the feeding tube 10 according to the present invention is illustrated in FIGS. 18 and 19, wherein FIG. 18 is a perspective view and FIG. 19 is a side view of the dilator portion 42 of the feeding tube 10. This embodiment comprises a coupling structure 26 similar to that illustrated in the embodiment of FIGS. 11 and 12. In particular, the coupling structure 26 comprises a clip mechanism 80 that includes a movable latch 82 that engages a stop 84, which together form a receiving area 86 configured to receive the loop 24 of a pull wire 22. More specifically, the latch 82 is movable between a closed position, shown in FIG. 18, and an open position wherein the latch 82 is spaced away from the stop 84. When in the open position, the latch 82 permits the loop 24 of a pull wire 22 to pass through the gap and into the receiving area 86. The latch 82 comprises a resilient material that is biased in the closed position, but which can be depressed into the open position by a user by, for example, depressing the latch 82 in an inward direction. The clip mechanism 80 allows the loop 24 of the pull wire 22 to be quickly secured to the dilator 42 of the feeding tube 10. This embodiment further includes a guiding structure 28 on the distal tip 54 of the dilator 42. The guiding structure 28 comprises a pair of grooves 88 formed in the distal tip 54 adjacent to the receiving area 86. Like the other embodiments described above, the grooves 88 help to guide the pull wire 22 towards the distal most portion of the distal tip 54.

Figure 20:
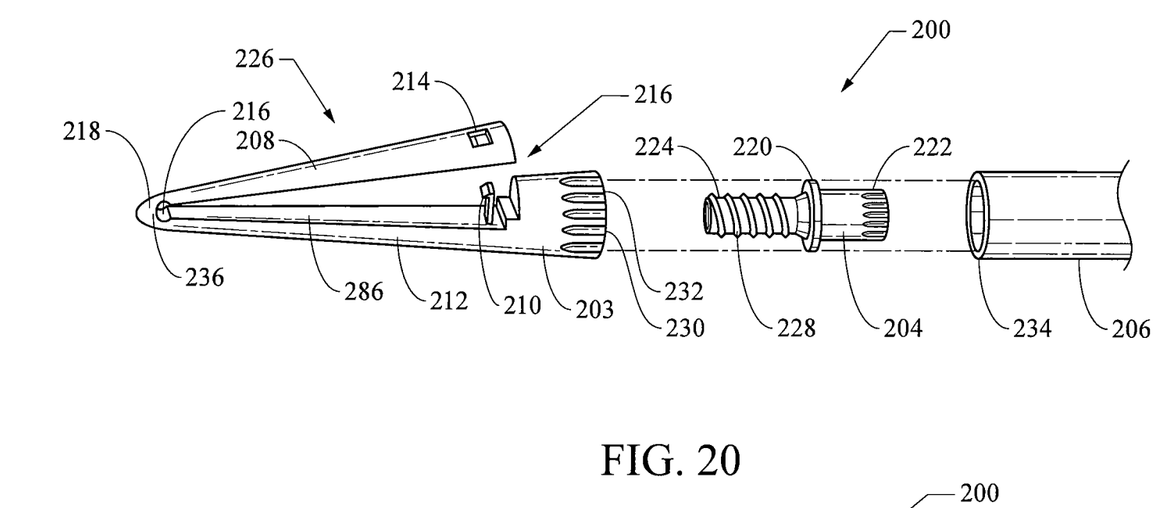
FIG. 20 is a perspective exploded view of a dilator assembly according to another embodiment of the present invention.
Figure 21:
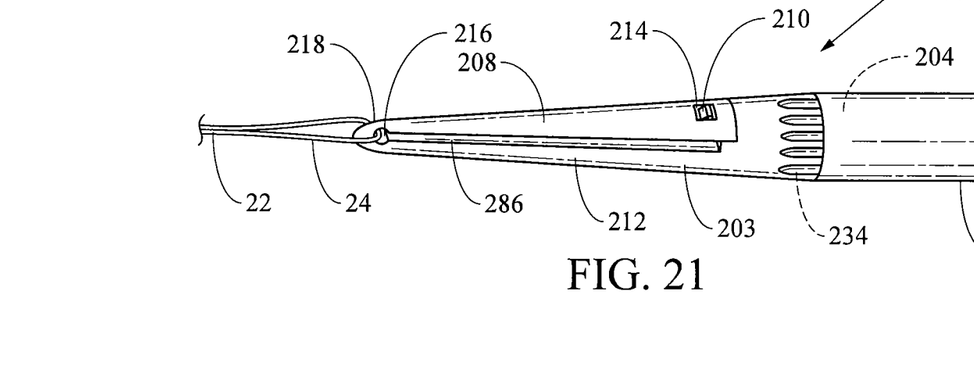
FIG. 21 is a perspective view of the dilator assembly of FIG. 20 assembled to the distal portion of a feeding tube.

Another alternative embodiment of the feeding tube 200 according to the present invention is illustrated in FIGS. 20 and 21. FIG. 20 is a perspective exploded view of a dilator assembly and the distal portion of the feeding tube prior to assembly of the feeding tube 200. FIG. 21 is a perspective view of the dilator assembly assembled to the distal portion of the feeding tube. As best seen in FIG. 20, the dilator assembly comprises a dilator tip 202 and an insert member 204 that are configured to couple the assembly to the distal end of the feeding tube shaft 206.

The dilator tip 202 comprises a coupling structure 226 similar to that illustrated in the embodiment of FIGS. 18 and 19. In particular, the coupling structure 226 comprises a first or upper arm 208 that is movably or pivotally connected to a second or lower arm 212 though a living hinge 236 disposed near the distal tip 218 of the dilator tip 202. The upper arm 208 is configured to engage a latch 210 disposed on the lower arm 212 of the dilator tip 202 when the upper arm 208 is moved into a closed position (as shown in FIG. 21). The upper arm 208 includes a cavity 214 that receives and engages with the latch 210 when the latch 210 is disposed therein so as to secure the upper arm 208 in closed configuration with the lower arm 212. In the particular embodiment illustrated, the latch 210 includes a transversely projecting tooth or ridge that is configured to engage a corresponding recess or lip on the inside surface of the cavity 214. However, other types of structures can be used to permit the latch 210 to engage with the cavity 214 in a secure manner. Moreover, other types of mechanisms other than the latch 210 and cavity 214 may be utilized to permit the upper arm 208 to be secured to the lower arm 212. For example, the upper arm 208 and the lower arm 212 could each comprise an outwardly projecting barb that are each configured to engage with the other.

The coupling structure 226 further comprises a receiving area 286 configured to receive the loop 24 of a pull wire 22 (shown in FIG. 21). More specifically, the upper arm 208 is movable or pivotal between an open position (shown in FIG. 20) and a closed position (shown in FIG. 21). When in the open position, the proximal end of the upper arm 208 is spaced away from the lower arm 212 a sufficient distance to permit the loop 24 of a pull wire 22 to pass through the gap 216 formed there between and into the receiving area 286. The distal end of the receiving area 286 comprises an expanded area 216 configured to secure the loop 24 of the pull wire 22 near the distal tip 218 of the coupling structure 226. In the particular embodiment illustrated, the expanded area 216 has a cross-section or width that is slightly larger than the cross-section or diameter of the loop 24, whereas the receiving area 286 has a width that is less than the cross-section or diameter of the loop 24 when the upper arm 208 is in the closed position. In some embodiments, the width of the receiving area 286 proximal of the expanded area 216 may be zero when the upper arm 208 is in the closed position. The expanded area 216 acts as a guiding structure to maintain the loop 24 in alignment with the distal tip 218 of the coupling structure 226. The distal tip 218 of the coupling structure 226 may further comprise grooves or other structures as described above in connection with the embodiment shown in FIGS. 18 and 19.

As shown in FIG. 20, the dilator tip 202 is assembled to the feeding tube shaft 206 via an insert member 204. The insert member 204 comprises an outwardly projecting flange 220 that is circumferentially disposed about a cylindrical body 222. The distal portion 224 of the body, i.e., distal of the flange 220, comprises an external thread 228. The distal portion 224 having the external thread 228 is configured to mate with an internal cavity 230 having an internal thread 232 disposed in the proximal end of the dilator tip 202. In other words, the distal portion 224 of the insert member 204 is configured to screwably mate with the proximal end of the dilator tip 202. The diameter of the flange 220 is somewhat smaller than the diameter of the internal cavity 230 so as to create a circumferential gap between these components. As will be explained in greater detail below, the width of this gap is sized to accommodate and frictionally engage the wall of the feeding tube shaft 206.

To assemble the dilator tip 202 to the feeding tube shaft 206, the insert member 204 is first disposed inside the distal end 234 of the feeding tube shaft 206. In particular, the insert member 204 is positioned such that the flange 220 is disposed within the feeding tube shaft 206 a short distance proximal of the distal end 234 thereof. The distal portion 224 of the insert member 204 is then screwed into the internal cavity 230 of the dilator tip 202 in such a manner as to frictionally engage and capture the distal end 234 of the feeding tube shaft 206 between flange 220 and the interior surface of the internal cavity 230. Once coupled, the distal end 234 of the feeding tube shaft 206 is disposed with the internal cavity 230 of the dilator tip 202, which provides a smooth transition between the dilator tip 102 and the feeding tube shaft 206. Glue may be applied to the external thread 228 and/or the internal thread 232 to prevent the distal tip 202 from uncoupling from the insert member 204. In the alternative, the distal tip 202 could comprise a proximally projecting tubular member having one or more barbs configured to be inserted into and frictionally engage with the distal end 234 of the feeding tube shaft 206. Other mechanisms for securing the dilator tip 202 to the feeding tube shaft 206 are also contemplated.

While there have been described what are presently believed to be the preferred embodiments of the invention, those skilled in the art will realize that changes and modifications may be made thereto without departing from the spirit of the invention. It is to be understood that the invention can be carried out by specifically different equipment and devices, and that various modifications, both as to the equipment details and operating procedures, can be accomplished without departing from the scope of the invention itself.

The invention claimed is:

1. A feeding tube apparatus for placement into the stomach of a patient using an elongate pull wire having a preformed loop attached to an end thereof, the feeding tube comprising:
    an elongate tubular portion having a feeding lumen extending through at least a portion thereof and configured to traverse a stoma through the patient's stomach and abdominal walls;
    a bolster fixedly connected to a proximal end of the tubular portion, the bolster having an enlarged cross-section configured to prevent egress thereof through the stoma; and
    a dilator portion connected to a distal end of the tubular portion and having a distal tip at the distal end thereof, the dilator portion comprising a coupling structure disposed proximal of the distal tip, the coupling structure including a receiving area configured to receive and secure the preformed loop of the elongate pull wire to the dilator portion,
    wherein the coupling structure comprises a first arm pivotally connected to a second arm and defining the receiving area there between, the first arm being movable relative to the second arm between an open position and a closed position, the open position providing external access to the receiving area and the closed position inhibiting external access to the receiving area, the coupling structure further comprising a latch mechanism configured to maintain the first arm in the closed position.

2. The feeding tube apparatus according to claim 1 wherein the first arm is connected to the second arm by a living hinge.

3. The feeding tube apparatus according to claim 2 wherein the living hinge is disposed near the distal tip.

4. The feeding tube apparatus according to claim 1 wherein the receiving area comprises a distal end having an expanded area configured to receive and retain the preformed loop of the pull wire therein.

5. The feeding tube apparatus according to claim 4 wherein the expanded area comprises a transversely oriented tubular passageway that is at least partially enclosed by the first and second arms when in the closed position.

6. The feeding tube apparatus according to claim 1 wherein the latch mechanism comprises a first engagement member disposed on the first arm and a second engagement member disposed on the second arm, the first engagement member being configured to releasably mate with the second engagement member in the closed position.

7. The feeding tube apparatus according to claim 6 wherein first engagement member comprises an outwardly projecting member disposed on a surface of the first arm and the second engagement member comprises an inwardly projecting cavity disposed in a surface of the second arm.

8. The feeding tube apparatus according to claim 1 wherein the latch mechanism comprises a proximal end portion of the first arm that is configured to releasably engage a groove formed in a transversely oriented surface of the coupling structure.

9. The feeding tube apparatus according to claim 8 wherein an outwardly projecting ridge is formed adjacent to the groove, the ridge being configured to inhibit movement of the proximal end portion of the first arm.

10. The feeding tube apparatus according to claim 1 further comprising an insert member disposed at least partially within the distal end of the elongate tubular portion, the insert member being coupled with a proximal end of the coupling structure such that the distal end of the elongate tubular portion is ensnared between the coupling structure and the insert member.

11. The feeding tube apparatus according to claim 10 wherein the insert member comprises a tubular body and a outwardly projecting flange circumferentially disposed about the tubular body, the flange being engaged with an interior surface of the elongate tubular portion, and further wherein the flange is disposed within a cavity in the proximal end of the coupling structure.

12. The feeding tube apparatus according to claim 11 wherein the tubular body comprises a distal portion having an external thread that is engaged with an internal thread in the cavity of the coupling structure.

13. The feeding tube apparatus according to claim 1 further comprising an elongate pull wire having a preformed loop disposed on an end thereof, wherein the preformed loop is disposed with the receiving area of the coupling structure and is capable of transmitting a distally directed pull force to the dilator portion of the feeding tube.

14. The feeding tube apparatus according to claim 1 wherein the apparatus comprises a percutaneous endoscopic gastrostomy feeding tube adapted for delivery of nutritional products directly into a patient's stomach, the tubular portion of the apparatus being adapted to extend percutaneously through the patient's abdominal and stomach walls, wherein the bolster comprises an internal bolster adapted to engage an interior wall of the patient's stomach, the apparatus further comprising an external bolster attached to the tubular portion distally of the internal bolster and adapted to engage an exterior wall of the patient's abdomen.

15. The feeding tube apparatus according to claim 14 wherein the dilator portion is tapered to facilitate ingress of the apparatus into the patient's gastrointestinal tract and out through the patient's abdominal and stomach walls, the dilator portion being removable after the tubular portion of the apparatus is extended percutaneously through the patient's abdominal and stomach walls.

16. A system for placement of a feeding tube apparatus into the stomach of a patient using an elongate pull wire having a preformed loop attached to an end thereof, the system comprising:

An elongate pull wire having a preformed loop fixedly connected to an end thereof;

an elongate tubular portion having a feeding lumen extending through at least a portion thereof and configured to traverse a stoma through the patient's stomach and abdominal walls;

a bolster fixedly connected to a proximal end of the tubular portion, the bolster having an enlarged cross-section configured to prevent egress thereof through the stoma; and a dilator portion connected to a distal end of the tubular portion and having a distal tip at the distal end thereof, the dilator portion comprising a coupling structure disposed proximal of the distal tip, the coupling structure including a receiving area configured to receive and secure the preformed loop of the elongate pull wire to the dilator portion, wherein the coupling structure comprises a first arm pivotally connected to a second arm and defining the receiving area there between, the first arm being movable relative to the second arm between an open position and a closed position, the open position providing external access to the receiving area and the closed position inhibiting external access to the receiving area, the coupling structure further comprising a latch mechanism configured to maintain the first arm in the closed position, and wherein the preformed loop is disposed with the receiving area of the coupling structure and is capable of transmitting a distally directed pull force to the dilator portion of the feeding tube.

* * * * *